United States Patent [19]
Dyrsting et al.

[11] Patent Number: 6,077,822
[45] Date of Patent: *Jun. 20, 2000

[54] DRUG SALTS

[75] Inventors: Hjarne Dyrsting, Virum; Torben Koch, Copenhagen, both of Denmark

[73] Assignee: Dumex-Alpharma A/S, Copenhagen, Denmark

[*] Notice: This patent is subject to a terminal disclaimer.

[21] Appl. No.: 08/402,619

[22] Filed: Mar. 13, 1995

Related U.S. Application Data

[63] Continuation-in-part of application No. 08/141,625, Oct. 27, 1993, Pat. No. 5,595,977, and a continuation-in-part of application No. 08/265,193, Jun. 24, 1994, Pat. No. 5,538,954, and a continuation-in-part of application No. PCT/DK94/00341, Sep. 13, 1994.

[30] Foreign Application Priority Data

Sep. 14, 1993 [DK] Denmark ................................. 1034/93
Jun. 10, 1994 [DK] Denmark ................................. 0667/94

[51] Int. Cl.$^7$ .......................... A61K 31/70; A61K 38/16; C07H 17/08; C07K 9/00
[52] U.S. Cl. .................. 514/8; 514/23; 514/53; 530/322; 536/7.1; 536/7.2; 536/13.8
[58] Field of Search ............................ 536/7.1, 7.2, 13.8; 514/23, 53, 8; 530/322

[56] References Cited

U.S. PATENT DOCUMENTS

| | | |
|---|---|---|
| 3,432,489 | 3/1969 | Nitta et al. . |
| 3,506,642 | 4/1970 | Koh et al. . |
| 5,116,821 | 5/1992 | Randall et al. . |

FOREIGN PATENT DOCUMENTS

| | | |
|---|---|---|
| 0 091 409 A1 | 10/1983 | European Pat. Off. . |
| 0 211 268 A3 | 2/1987 | European Pat. Off. . |
| 0 403 048 A2 | 12/1990 | European Pat. Off. . |
| 1227830 | 4/1971 | United Kingdom . |
| 1 305 860 | 2/1973 | United Kingdom . |
| WO 89/07932 | 9/1989 | WIPO . |
| WO 92/18143 | 10/1992 | WIPO . |

OTHER PUBLICATIONS

G. Delpre, MD et al.; "Induction of Esophageal Injuries by Doxycycline and Other Pills"; *Digestive Diseases and Sciences*; vol. 34, No. 5, pp. 797–800 (May 1989).

H. Yoshikawa et al.; "Development of Bifunctional Delivery System for Selective Transfer of Drug into Lymphatics Via Enteral Route and Transfer Mechanism"; *J. Pharm. Dyn.*; 5,S–69 (1982).

D. Mihai et al.; "Macromolecular Drug Conjugates Propranolol–Cation Exchangers Drug Delivery Systems"; *Cellulose Chemistry and Technology*; 27, pp. 393–403 (1993).

K. Ochi et al.; "Crystalline Salts of Sucrose Octasulfate"; *Chem. Pharm. Bull.*; vol. 28; pp. 638–641 (1980).

J. Jesper et al.; "Brief Report—In Vitro Susceptibility of *Campylobacter Pyloridis* to Cimetidine, Sucralfate, Bismuth and Sixteen Antibiotics"; *Acta. path. microbiol. immunol. scand.*; Sect. B, 95; pp. 147–149 (1987).

*Primary Examiner*—Elli Peselev
*Attorney, Agent, or Firm*—Watov & Kipnes, P.C.

[57] ABSTRACT

It has been found that sugar acid salts represent beneficial controlled release forms for basic organic drug compounds. Examples of appropriate salts include mono, di, oligo and polysaccharide poly-O-sulphonic acid salts of antibiotics such as tetracyclins and aminoglycosides.

19 Claims, 3 Drawing Sheets

DRUG SALTS

RELATED CASES

This is a continuation-in-part of U.S. patent application Ser. No. 08/141,625 filed Oct. 27, 1993 now U.S. Pat. No. 5,595,977 and Ser. No. 08/265,193 filed Jun. 24, 1994, now U.S. Pat. No. 5,538,954.

FIELD OF THE INVENTION

This invention relates to salts of biologically active organic molecules (drugs) with sugar acids, in particular salts with mono-, di- and oligosaccharide poly-O-sulphonic acids.

BACKGROUND OF THE INVENTION

It is common practice in the pharmaceutical industry to use salt forms of drugs, e.g. salts with physiologically acceptable organic or inorganic acids and bases, such as hydrogen chloride, sulphuric acid, maleic acid, ethanolamine, meglumine and the like. For drugs with basic groups, e.g. amine groups, it is feasible to use salts with organic or inorganic acids.

The drug salts are frequently used in preference to the drug itself, for example because of their higher solubility or greater biotolerability.

Many alkaline drug compounds cause irritation of tissue or mucosa. In particular, high local concentration can cause severe irritation and ulceration of the oesophagus. These compounds may also have an unpleasant taste and accordingly they can be administered provided with a polymeric film coating to delay drug release. Such coatings however add to the cost and complexity of formulation.

The present invention is based upon the finding that drug salts with sugar acids exhibit surprising beneficial properties, in particular enhanced uptake and controlled release properties. In particular, insoluble or poorly soluble drug:sugar acid salts have been found to have a drug release profile which is not undesirably dependent on the pH of the surrounding body fluid, eg gastrointestinal fluid.

By the term "sugar acids" is meant herein mono-, di-, oligo- and poly-saccharides (such as xylose, fructose, glucose, sucrose, lactose, maltose, cellobiose, trehalose, sorbitol, mannitol and dextran) which carry oxyacid groups on the saccharide moieties (eg carboxyl groups or esters or oxyacids, such as phosphorus and sulphur oxyacids, with the sugar hydroxyls), which sugar acids, in the case of the polysaccharides (and preferably also the oligosaccharides, disaccharides and monosaccharides), contain a high ratio of acid groups to monosaccharide units, ie at least 2:1, preferably at least 3:1. Such sugar acids have been used in various medicaments but have not previously been proposed for use in forming salts of organic drug compounds.

SUMMARY OF THE INVENTION

Thus viewed from one aspect the invention provides a therapeutic compound being sugar acid salt of a biologically active organic molecule, preferably the salt with a polybasic sugar acid, especially a mono or disaccharide poly-O-sulphonic acid.

The sugar acid used according to the invention is preferably a carboxylic acid or a sulphate or phosphonate ester, particularly a sulphate, of a mono-, di- or trisaccharide, in particular a polyester or perester, i.e. a compound in which more than one and optionally all of the sugar hydroxyls are esterified, preferably a compound carrying at least 2, and especially at least 3 oxy-acid groups per saccharide unit.

The disaccharide sulphonic acids are especially preferred, in particular the sucrose sulphonic acids such as sucrose-octa-O-sulphonic acid (SOS).

The drug may be any organic drug compound capable of forming a sugar acid salt, in particular a compound containing an electron donor base group such as a basic nitrogen atom, e.g. an amine, imine or ring nitrogen. The drug compounds preferably contain one or more exposed protonatable amine functionalities, particularly preferably a plurality of such groups. Drug compounds useful in the production of the poorly water soluble drug:sugar acid salts of the invention include antibacterial agents (in particular tetracyclins, aminoglycosides, glycopeptides, polypeptides and macrolides), antiviral agents, antimycotics, antiamoebics, anti-allergics (such as antihistamines), analgesics, anxiolytics, sedatives, hypnotics, anti-emetics, anti-migraine agents, anti-motion sickness agents, antidepressants particularly tricyclic antidepressants (such as imipramine, amitriptyline and doxepin), alkaloids, cardioprotective agents (such as calcium antagonists, eg diltiazem, and azepine derivatives), adrenergics, anticholinergics, antispasmodics, antianorexics, and muscle relaxants, particularly the tricyclic muscle relaxants (eg cyclobenzaprine and benzoctamine).

The drug sugar acid salt particularly preferably has a low water solubility, for example less than 10 g/L, preferably less than 1 g/L more preferably less than $10^{-2}$ mM/L, in deionized water at ambient temperature. This poor water solubility both imparts favourable biorelease characteristics and facilitates preparation of the salts by precipitation from aqueous solution.

The drug compound may be, and preferably is, polybasic and the sugar acid, as mentioned above, is preferably a poly or perester which is thus also polybasic. Accordingly the drug salt of the invention may contain further physiologically tolerable counterions. In this regard alkali and alkaline earth metal (e.g. sodium, potassium, magnesium and calcium), aluminum and ammonium and countercations derived from organic bases such as ethanolamine, diethanolamine and meglumine are preferred cations, while bromide, chloride, sulphate, maleate, acetate, fumarate, succinate and other physiologically tolerable anions derived from inorganic or organic acids are preferred anions.

In the solid state, the drug salts of the invention are amorphous or crystalline materials, preferably presented in sterile form.

The drug salts of the invention may be formulated together with conventional pharmaceutical carriers or excipients, optionally together with further bioactive agents, in conventional pharmaceutical administration forms, e.g. powders, capsules, tablets, coated tablets, suspensions, dispersions, drops, aerosols, suppositories, plasters, pastes, creams, emulsions, etc. These are preferably in sterile form.

Accordingly, viewed from a further aspect the invention provides a pharmaceutical composition comprising a biologically active organic compound together with at least one physiologically acceptable carrier or excipient, the improvement consisting in that said compound is in the form of a salt with a sugar acid.

Viewed from a yet further aspect the invention also provides a method of treatment of a warm-blooded animal, eg a human or a non-human mammal, with an effective amount of a biologically active organic compound to combat a condition responsive to said compound, said method comprising administering to said warm-blooded animal an effective amount of said organic compound in the form of a salt with a sugar acid.

BRIEF DESCRIPTION OF THE DRAWINGS

In the accompanying drawings.

DETAILED DESCRIPTION OF THE INVENTION

Sugar acids are produced by esterification of a mono-, di-, oligo- or poly-saccharide with a polybasic oxyacid (e.g. a phosphorous or phosphoric acid or a sulphur oxyacid such as sulphurous or more preferably sulphuric acid) or an activated analog thereof (such as sulphur trioxide). One or more, and preferably most or all of the sugar's hydroxyl groups are esterified to yield oxygen-attached acid groups such as O-sulphonic acid groups.

The sugar acid conveniently has a molecular weight of up to 1000 kD. Preferably however the molecular weight is below 1500 kD, and especially below 30 kD. Mono-, di- and oligosaccharides having up to 100, particularly no more than 8, especially 1, 2 or 3, monosaccharide units are particularly prefered.

The sugar acids are known compounds and are discussed for example by Ochi et al in Chem Pharm Bull 28:638–641 (1980) and WO89/07932 (Niels Bukh A/S).

Preferred among the sugar acids useful according to the present invention is the sulphate octa-ester of sucrose, β-D-fructofuranosyl-α-D-glucopyranoside octakis (hydrogen sulphate), hereinafter referred to as sucrose-octa-O-sulphonic acid or SOS.

SOS may be prepared by sulphating sucrose with sulphur trioxide in pyridine. SOS forms crystalline, water soluble sodium, potassium, caesium, rubidium and ammonium salts as reported by Ochi (supra).

SOS also forms an aluminum salt, $C_{12} H_{54} Al_{16} O_{75} S_8$, which is known as sucralfate. This aluminum salt may be prepared by reaction of SOS with aluminum hydroxide (see U.S. Pat. No. 3,432,489 (Chugai)) and is widely used for the treatment of gastric ulcers, its effectiveness being ascribed to the aluminum hydroxide ions which act as acid neutralizers and absorb pepsin and bile salts (see Nagashima in Clin. Gastroenterol 3(Suppl. 2):117–227(1981)).

Although no medical used for sugar acid salts with bioactive organic counterions have been proposed, there have been several suggestions for the coadministration of sugar acids or their metal salts together with bioactive agents. Thus for example WO89/07932 (Niels Bukh A/S) describes sugar acid metal salts as ingredients for a topical preparation for periodontal treatment, EP-A-403048 (Warner Lambert) discloses admixtures of sucralfate with other anti-ulcer agents, and WO92/18143 (Smith Kline Beecham Plc) discloses admixtures of sucralfate with various antibiotics.

The drug salts of the invention are generally suited for use where controlled release of the active drug is desired, e.g. for topical administration especially to mucous membranes or administration, preferably per oral, into the gastrointestinal tract.

A particularly valuable characteristic of the salts according to the invention is their ability to release the drug when placed in an ion containing aqueous environment such as gastrointestinal fluid, essentially it appears as a result of ion exchange with competing cations such as sodium or magnesium that are present in the body fluid.

One particularly suitable group of drug compounds for use according to the invention are the antibiotics, in particular basic nitrogen atom containing antibiotics, such as aminoglycosides, tetracyclins, polypeptides, macrolides and glycopeptides.

One preferred group of antibiotic drugs with which to form the sugar acid drug salts of the invention is the amino glycosides. Examples of suitable aminoglycosides include amikacin, apramycin, arbekacin, bambermycins, butirosin, dibekacin, dihydrostreptomycin, fortimicin, gentamicin, isepamicin, kanamycin, micronimicin, neomycin, netilmicin, paromycin, ribostamycin, sisomicin, streptomycin and tobramycin. Amikacin, gentamicin, kanamycin, neomycin, streptomycin and tobramycin are particularly preferred.

The aminoglycoside:sugar acid salts are particularly suitable for use in the treatment of ulcers, especially stomach or duodenal ulcers and particularly ulceration associated with *Helicobacter pylori*.

*Helicobacter pylori* (previously known as *Campylobacter pylori*) is a helical Gram-negative organism which is present in the stomach mucosa. Many recent tests have shown a clear correlation between the presence of *H. pylori* in the stomach mucosa and histologically demonstrated gastritis. This seems to indicate that this organism is wholly or partially responsible for the development of gastritis with ensuing ulcerations (see Scand. J. Gastroenterol. (1988) 23 suppl. 142, pages 93–100).

*H. pylori* is sensitive to a number of known antimicrobial substances in vitro. Furthermore, several publications disclose that the treatment of gastritis with antimicrobial agents, such as β-lactams (e.g. amoxicillin) or bismuth salts can result in the eradication of *H. pylori* in vivo (see Antimicrobial Agents and Chemother. 1993, pages 1184–86).

The traditional treatment of ulceration in the human stomach or the duodenum involves administering acid neutralising agents or anti-histamines of the H2-inhibitor type (e.g. ranitidine, cimetidine, etc.) which reduce the production of acid, and acid pump-inhibitors, such as omeprazole. This treatment as such is efficient, but it has a short-term effect only as, in almost every case, there is a relapse due to *H. pylori* infection still being present.

Today the optimum treatment of ulceration caused by *H. pylori* involves combined administration of bismuth subcitrate, amoxicillin and metronidazole. This treatment cures 60–90% of the patients (see Ann. Rev. Med. 1992 (43) page 142).

However, there are certain side effects associated with this therapy: bismuth subcitrate may cause constipation and in large doses it may be neurotoxic; and amoxicillin and metronidazole are systemically acting antibiotics which may cause development of allergy or resistance and influence the microflora in the colon.

Therefore, there is a continuing need for a preparation for local treatment of *H. pylori* infection in the stomach and the duodenum.

Amino glycosides are a group of antibiotics which have a good in vitro effect on *H. pylori*. The following MIC-values are known from the literature:

TABLE 1

| | Average MIC 90 range |
|---|---|
| AMIKACIN | 0.5 |
| GENTAMYCIN | 0.04–1 |
| KANAMYCIN | 0.04–2 |
| STREPTOMYCIN | 0.04–1.28 |
| TOBRAMYCIN | 0.04–0.64 |

(see Antimicrobial Agents and Chemother., 1986, pp. 510–511, J. Antimicrobial Chemother. 1986, 17 pp. 309–314, and Scand. J. Gastroenterol., 1988, 23 (suppl. 142), pp. 93–100).

Thus far however amino glycosides have not been found to be suitable for use in the treatment of *H. pylori* infections because they are not absorbed following peroral administration of therapeutic doses. When readily soluble salts of amino glycosides are administered orally, they do not influence the stomach and duodenum mucosae due to their poor tissue penetration and thus are not capable of eradicating *H. pylori*. Instead they will have a considerable influence on the colon microflora and may cause diarrhoea. Amino glycosides could be administered parenterally in ulcer treatment but this is impractical as they have known oto- and nefrotoxic properties.

Amino glycosides belong to the group of sugars having a number of amino groups, preferably 4, 5 or 6. They are obtained by fermentation of various Streptomyces- or Micromonospora-species. Due to the many hydrophilic hydroxy or amino groups in the amino glycosides they and the normally used pharmaceutical salts thereof are readily soluble in water.

As the amino glycosides and the sugar acids are generally polybasic it is not immediately predictable that they should together form low water solubility salts.

The drug:sugar acid salts of the invention may be described by the general formula where D, SA and CA respectively represent the drug molecule (or a cation thereof), the sugar acid (or an anion thereof) and a physiologically tolerable counterion, a and b are positive numbers (not necessarily integers), and c is zero or a positive number.

By way of example the aminoglycoside SOS salts can be represented by the formula (I)

where $R(NH_2)_x$ is the aminoglycoside (preferably a mono-, di- or trisaccharide), $M^{n+}$ is a pharmaceutically acceptable cation, preferably alkali metal, alkaline earth metal, aluminum or ammonium ions, x is an integer having a value of from 1 to 6,
n is an integer having a value of from 1 to 3,
z is zero or a positive number having a value of up to 4,
y is a positive number having a value such that the product of y and x is from 4 to 8, and the sum of the product of x and y and the product of n and z is 8.

It has been found that it is possible to form well defined compounds between sucrose-octa-O-sulfonic acid and an amino glycoside and then to produce mixed salts by introducing cations. The following pharmaceutically acceptable cations are preferred: alkali metal ions, such as $Na^+$ and $K^+$; ammonium; alkaline earth metal ions, such as $Ca^{2+}$ and $Mg^{2+}$; and aluminum.

The novel drug:sugar acid salts according to the invention preferably have comparatively low solubility in water, such that when stirred into water they form oily or sticky gels with a high degree of affinity to the inside surface of the container. They will preferably also have this affinity for biological surfaces such as the mucosae of the stomach or the duodenum.

Furthermore, the novel salts will preferably release the drug compound in aqueous solutions at a low pH. Therefore, the aminoglycoside salts for example will be suitable for the treatment of ulceration in the stomach and the duodenum caused by *H. pylori*.

By peroral administration in a suitable pharmaceutical formulation, the novel aminoglycoside salts produce a gel which covers the mucosae of the stomach and/or the duodenum when the stomach pH is neutral or slightly below neutral.

Upon consumption of food, the stomach will secrete hydrochloric acid. *H. pylori* is sensitive to acid, such as gastric acid, but it has developed a protective measure. This protective measure consists of *H. pylori* producing an enzyme, urease, which splits urea into ammonia and $CO_2$. The ammonia thus formed neutralizes the gastric acid.

When the areas of the stomach which are infected with *H. pylori* come into contact with the aminoglycoside salts according to the invention, the ammonia formed causes release of the amino glycoside which subsequently kills the *H. pylori*.

If insufficient ammonia to neutralize the gastric acid is formed, the gastric acid will itself release the amino glycoside from the novel salts.

A further exemplary group of the drug compounds which can be presented according to the invention as their sugar acid salts are the tetracyclin antibiotics, a preferred example being doxycyclin.

For more than 50 years tetracyclins have been used as antibiotics. By the term "tetracyclin" is meant an antibiotic of the class containing the fused tetracyclic ring system of tetracyclin itself:

The tetracyclins belong to a group of antibiotics which are manufactured by fermentation of various Streptomyces species. The most widely used are doxycyclin, oxytetracyclin, chlorotetracyclin and tetracyclin. A number of semisynthetic tetracyclins are known, for instance metacyclin and minocyclin. The most widely used of these semisynthetic tetracyclins is α-6-deoxy-5-hydroxy-tetracyclin (doxycyclin). This broad-spectrum antibiotic was first synthesised in 1962 and is marketed by Pfizer under the name Vibramycin®.

Doxycyclin is available in several different forms: doxycyclin monohydrate, doxycyclin hydrochloride (hyclate), doxycyclin carrageenate, doxycyclin calcium and doxycyclin phosphate (fosfatex).

Doxycyclin has a mode of action which is common with other tetracyclins, namely inhibition of bacterial protein synthesis. This arises through inhibition of the binding of aminoacyl-tRNA primarily to 70S ribosomes but also to 30S ribosomes. This results in a bacteriostatic effect. Tetracyclins are active against a broad range of both gram positive and gram negative bacteria, aerobes as well as anaerobes.

Bacterial resistance to tetracyclins is common both in vitro and in vivo, and the resistance is transferred by a plasmid. Due to the bacteriostatic effect of the tetracyclins they usually can not be combined with other cell-cycle specific antimicrobial agents, as the resting cells do not change cell cycle.

Most tetracyclins are incompletely absorbed and their absorption is dependent on the concomitant food intake. Absorption of doxycyclin however is almost complete (73–95%) and independent of food intake (see Saivin et al. in Clin. Pharmacokinetics 15:355–366 (1988)).

The pharmacokinetic parameters of the different salts (hyclate, monohydrate, carrageenate etc.) of doxycyclin do not significantly differ under standard conditions (see Saivin et al. (supra) and Grahnén "Effect of increasing gastric pH on the relative bioavailability of doxycyclin carageenate tablets 100 mg (Kabi Pharmacia) in comparison", Internal Study Report, PCB, Sweden, (1991)).

Two factors have been reported which influence the pharmacokinetics of doxycyclin. The pH in the stomach (see Grahnén (supra)) and the concomitant administration of oral antacids (see Nguyen in Antimicrob. Agents Chemother. 33:434–436(1989)).

An increased pH of the stomach (see Bogardus et al. in J. Pharm Sci 68:1183–1184(1979)) decreases the bioavailability of doxycyclin monohydrate whereas dissociation and absorption of doxycyclin hyclate and doxycyclin carregeenate are independent of pH.

The increased pH in the stomach after omeprazole administration is thus expected to slow down the dissolution of doxycyclin monohydrate and thereby decrease its absorption.

Doxycyclin was first introduced into chemical practice in 1968 as the hydrochloride salt, doxycyclin hyclate. This salt was formulated in tablets or capsules. However, it was soon shown that these formulations had serious side effects. In a study of adverse drug reactions from antibiotics, 35/113 (31%) of patients treated with doxycyclin hyclate after questioning reported nausea and vomiting while 24/373 (6.4%) spontaneously reported nausea and vomiting. These frequencies were 3-fold higher than those reported with other antibiotics.

Another side effect of doxycyclin hyclate is oesophageal ulceration, which can occur if the capsules for some reason do not reach the stomach but remain in the oesophagus.

A solution to these problems has been attempted by the introduction of doxycyclin hydrate (base). This new formulation eliminated the above mentioned side effects, but it soon became apparent that the bioavailability in a number of patients, which were also in treatment with antacids and the like, was significantly reduced. This can be explained by the lack of acid production in the stomach being the cause of reduced dissolution of doxycyclin hydrate.

Considering that a great deal of the population has elevated gastric pH caused by either achlorhydria or due to the intake of antacids, H2-blockers, omeprazole or the like, antibiotic treatment with doxycyclin hydrate gives an unacceptably low bioavailability.

One solution to this problem has recently been suggested by the introduction of doxycyclin carrageenate, which has a satisfactory bioavailability in subjects with elevated gastric pH. In subjects with normal pH conditions in the stomach, the use of doxycyclin carrageenate has no advantage due to the spontaneous cleavage of doxycyclin carrageenate into doxycyclin H$^+$ and carrageenate ion.

By using different pharmaceutical preparations of doxycyclin, attempts have been made to achieve a controlled release effect.

One solution has been the use of film coated tablets. A coated doxycyclin hyclate formulation was developed which showed less tendency to disintegrate in the oesophagus (see Delphre et al. in Digestive Disease and Sciences 34:197–800 (1989)). An enteric coated pellet formulation of doxycyclin (sold under the names Doryx® and Doxylets®) has been developed to prevent the total dose of doxycyclin hyclate dissolving in a small area of the stomach. Such formulations have been shown to have a reduced (approximately 50% reduction) rate of nausea and vomiting and an unchanged bioavailability. A pellet formulation however does not automatically have an unchanged bioavailability. In a doxycyclin pellet formulation developed at the university of Nanking, China, it was found that 200 mg of the pellet formulation were bioequivalent to 100 mg of the standard doxycyclin hyclate formulation (see Qiu et al. in Acta Pharm. Sinica 21:370–376(1986)). Therefore a need still exists for tetracyclin and particularly doxycyclin formulations with controlled release properties.

In EP-A-91409 (Kabi Vitrum) complexes between carrageenan and three drug compounds are described. Carrageenan is a sulphated polysaccharide with a molecular weight from 100 kD to 1000 kD which carries a low density of sulphate groups per saccharide unit. Complexes of Aubygum x2 (a mixture of kappa and lambda carrageenans) with doxycyclin, emepronium and propanolol were disclosed. The doxycyclin complex is insoluble in water, but in the gastric juice doxycyclin is released at the same rate as from the soluble doxycyclin hyclate. The drug release profile however is strongly pH dependent.

The sulfosalicylate of doxycyclin is known from GB-A-1305860 (Alfa Farmaceutici). This salt is sparing soluble in water and is used in the doxycyclin manufacturing process. The sulfo-salicylic acid salt however has no clinical use, as sulfosalicyclic acid is not accepted for medicinal use.

It has now surprisingly been shown that tetracyclins form sparingly soluble salts with sugar acids, salts which can be used for the controlled release of the tetracyclin antibiotic within the gastrointestinal tract.

The salts with SOS are crystalline and particularly preferred. These can be described by the following formula:

wherein TC is a tetracyclin molecule, and x is a number of from 0 to 20 indicating the amount of water which forms a hydrate with the new salt or which is physically bound to the new salt.

Other examples of amine group containing antibiotics which can be used to form poorly water soluble drug:sugar acid salts according to the invention include polypeptides (such as bacitracin and polymyxin), glycopeptides (such as vancomycin), and macrolides (such as erythromycin and oleandomycin), streptomycins and penicillins.

These poorly water soluble salts can again advantageously be used to achieve controlled release of the antibacterial agent within the gastrointestinal tract, e.g. following peroral administration.

The drugs usable in this fashion are not restricted to the antibiotics and indeed poorly water soluble salts can be produced with a wide range of acid salt forming drug compounds, for example neuroleptics, antidepressants, eg tricyclic antidepressants (such as imipramine), the structurally related tricyclic muscle relaxants (such as cyclobenzaprine), antichlorinergics, antihistamines, antianorexics, cardioprotective azepine derivatives (such as benzothiazepinones like diltiazem), and alkaloids (such as the antitussive agent noscapine).

Further drug categories which may be considered include antivirals (such as acyclovir, idoxuridine and tromantadine), antimycotics (such as miconazole, ketoconazole, fluconazole, itaconazole, econazole, terconazole, and polyenes such as amphotericin B or mystatin), anti-amoebics (such as metronidazole and tinidazole), antihistamines (such as diphenylhydramine, chlorpromazine, pyrilamine and phenyltoloxamine), calcium agonists (such as verapamil and nifedipine), anxiolytics, sedatives and hypnotics (such as benzodiazepines, diazepam, nitrazepan, flurazepam, estazolam, flunitrazepam, triazolam, alprazolam, midazolam, temazepam, lormetazepam, brotizolam, clobazam, clonazepam, lorazepam and oxazepam), antimigraine agents (such as sumatriptan), anti-motion sickness agents (such as cinnarizine), anti-emetics (such as ondansetron, tropisetron and granisetrone), adrenergics (such as amphetamine), antispasmodics (such as aminopentamide, metixene and dicyclomine), ataractics (such as benactyzine), antihypertensives (such as hexamethonium and pentamethonium), analgesics and alkaloids (such as 2,6-diamino-3-phenyl-azopyridine, morphine, papaverine and ethaverine), antitussives (such as dihydrocodeine, phenylpropenolamine, guaiacol, cloperastine and dextromorphen), bronchodilators (such as dimethylephedrine), antipsychotics (such as imipramine), coronary dilators (such as etafenone), antiarrhythmics (such as procainamide), hypotensives (such as hydralazine and clonidine) and peripheral vasoconstrictors (such as tolazoline).

Further examples of amine containing drug compounds include acetophenazine, amitriptyline, bromopheniramine, carbinoxamine, chlorcyclizine, cyclizine, desipramine, dexbrompheniramine, dexchlorpheniramine, ergotamine, nortriptyline, quinidine, benztropine, flunarizine, fluphenazine, hydroxychloroquine, hydroxyzine, meclizine, mesoridine, methdilazine, methysergide, pheniramine, pyrilamine, tripelennamine, triprolidine, promazine and quinidine.

The new drug:sugar acid salts may be prepared particularly simply by containing a water soluble form of the drug, either the free base or a water soluble salt thereof (e.g. a hydrochloride), with a water soluble form of the sugar acid, optionally in the presence of further counterions which it is desired to precipitate as part of a drug:sugar acid mixed salt. Contacting will generally be effected in a solvent or solvent mixture, optionally a water-miscible solvent system in which drug, sugar acid and salt are all soluble in which case salt precipitation may be effected by addition of water.

Various basic drug compounds do not form water-insoluble sugar acid salts; however it is of course readily determined by simple experimentation whether or not a poorly soluble salt forms.

In general, if a 100 mM solution of the drug hydrochloride in ion-exchanged water is mixed with an equinormal amount of sugar acid (ie an acid group:drug molecule ratio of 1:1) also in solution in ion-exchanged water, eg in a volume about ¾ of that of the drug solution, a poorly soluble drug:sugar acid salt would precipitate out.

The novel salts are particularly advantageously produced by allowing an aqueous solution of the drug base to react with an aqueous solution of sugar acid by titration to obtain the desired stoichiometric ratio.

If it is desired to produce salts in a 1:1 ratio it may be necessary to neutralise excess acid groups in the sugar acid with suitable cations, such as $Na^+$, $Ca^+$, $Mg^{2+}$ or $Al^{3+}$. In many instances, the salts thus formed will crystallize spontaneously. If this is not the case the salt may be obtained by evaporation, optionally to dryness, or by freeze drying, or by additional of a solvent which is miscible with water, such as methanol or ethanol.

By way of example, a soluble aminoglycoside (e.g. kanamycin A) may be dissolved in water and a solution of SOS may be added thereto. The drug:sugar acid salt separates out as a syrup which can be crystallized from ethanol.

As a further example, to a solution of a tetracyclin (e.g. doxycyclin) in hydrochloric acid there may be added an aqueous solution of SOS-sodium salt. The drug:sugar acid salt precipitates out.

Where inclusion of aluminum as a counterion is desired, the initial aluminum containing aqueous solution should be at a low pH, e.g. about 4, and the precipitation is accomplished by raising the pH, eg to 5.5 to 6. The aluminum salt solution may be brought into contact with the drug or drug salt before the sugar acid is added if the drug or drug salt will remain stable in solution in that environment. Otherwise all three components may be brought together simultaneously, optionally with subsequent addition of a base to raise the pH to complete precipitation.

A further option is to effect ion exchange between aluminum, in an insoluble aluminum sugar acid salt, and the drug cations. This requires careful pH control, e.g. to about pH 4, to ensure the exchange reaction occurs.

Thus it is possible to use sucralfate as a starting material. In this case, by way of example the chosen drug is dissolved in water and the pH is adjusted to 4.0. To this solution, an equivalent amount of sucralfate is added with vigorous stirring. An ion exchange reaction takes place whereby the drug forms ion bonds with one or more of the sulphonic acid groups in sucrose-octa-O-sulphonic acid and a corresponding amount of aluminum passes into the aqueous phase. When the reaction is completed the novel salts are filtered off and washed with water.

This reaction will only take place in a very narrow pH range, i.e. around pH 4. If pH is higher than 4, the Al-ion is not dissolved and, therefore, it cannot be separated form the reaction product by filtration. If pH is lower than 4, a gel formation takes place which also makes a separation impossible. Furthermore, at too low a pH, the equilibrium may move in such a manner that the drug will remain dissolved.

Thus viewed from a further aspect the invention provides a process for the preparation of poorly water-soluble sugar acid salts of bioactive organic compounds, said process comprising reacting salt compound or a salt thereof with said acid or a salt thereof in a solvent system and separating said salt from said system, e.g. by filtration.

The salts can be obtained directly, on via recrystallation, as surprisingly poorly-soluble, well crystallized material.

Because of the new salts' low solubility in water, the main part of the active drug will be bound to the sugar acid moiety and thus remain biologically inactive during the passage of the oesophagus. This greatly reduces the risk of unfavourable interaction with the mucosa in the oesophagus.

When pharmaceutical formulations are made which contain the new salt for oral use, or peroral administration, the salt can be mixed with a solid pulverised carrier, such as: calcium carbonate, calcium phosphate, calcium crospovidone sulphate, microcrystalline cellulose, cellulose dextrates, dextrin, dextrose excipient, fructose, lactose, mannitol, sorbitol, starch providone, pregelatinized starch, sucrose, compressible sugar or confectioner's sugar; and can also contain lubricants, such as: calcium stearate, magnesium stearate, polyethylene glycol, stearic acid, talc, or zinc stearate. A tabletting mixture may be prepared and mixed with other subsidiary materials before being compressing it into tablets. If coated tablets are desired, then the core—made as outlined above—might be coated with: sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methylacrylic acid copolymer, methylcellulose, polyethylene glycol, polyvinyl acetate phthalate, shellac, sucrose, titanium dioxide, carnauba wax, microcrystalline wax or zein which is first dissolved in water an organic solvent or a mixture of solvents. Colouring agents can be added to this dissolution, so that tablets with different strengths can be identified.

Powders and granulates can be made, which contain the new salt alone or mixed with a solid pulverulent carrier, such as: calcium carbonate, calcium phosphate, calcium crospovidone sulphate, microcrystalline cellulose, cellulose, dextran, dextrin, dextrose excipient, fructose, lactose, mannitol, sorbitol, starch providone, pregelatinized starch, sucrose, compressible sugar, or confectioner's sugar; and can also contain lubricants, such as: calcium stearate, magnesium stearate, polyethylene glycol, stearic acid, talc, or zinc stearate. The remainder can be comprised of, for example, sweetening agents, such as sugar, aspartame, dextran, dextrose, fructose, mannitol, saccharin, calcium saccharin, sodium saccharin, sorbitol or sucrose.

The powders or granulates may be dissolved and/or dispersed before use. They may also be mixed with a foodstuff before administration.

Soft gelatin capsules can be made, which contain a mixture of the salt and/or vegetable oil. Hard gelatin capsules can contain granulates of the salt in combination with a solid pulverulent carrier such as: calcium carbonate, calcium phosphate, calcium crospovidone sulphate, microcrystalline cellulose, cellulose, dextran, dextrin, dextrose excipient, fructose, lactose, mannitol, sorbitol, starch, povidone, pregalatinized starch, sucrose, compressible sugar, or confectioner's sugar, or the new salt alone; and can also contain lubricants, such as: calcium stearate, magnesium stearate, polyethylene glycol, stearic acid, talc, or zinc stearate.

Liquid formulations which may be used for oral use, or peroral administration, may be made in the form of syrups, suspensions, emulsions, or mixtures which can contain up to approximately 20% of the new salt. The remainder can be comprised of, for example, sweetening agents, such as sugar, aspartame, dextran, dextrose, fructose, mannitol, saccharin, calcium saccharin, sodium saccharin, sorbitol or sucrose and a mixture of diluents, like ethanol, water, glycerol and propylene glycol.

The dose in which the new salt is administered is dependant on different factors, like for example the nature of the drug compound and individual needs and administration preferences of each patient. The dosages will generally be on the same level as normally used for the drug compound.

By way of example, dosage units containing 1 to 100 mg, conveniently 50 to 200 mg, and preferably about 100 mg of the drug compound per unit will be preferred.

For doxycyclin salts, for example, dosages of 100 to 400 mg/day of the drug compound will normally be required. As a further example, for the amine glycosides, it will be preferred to administer the novel salts in tablets or capsules which disintegrate in the stomach or duodenum and which each contain from 50 to 250 mg, preferably about 100 mg, of the amino glycoside together with conventional adjuvants and/or carriers.

The dissolution properties of the new salts according to the invention can easily be demonstrated by the method described in the Examples below.

By modifying the composition of the new salts according to the invention, it is possible to change the dissolution properties in order to optimize the compositions with regard to the dissolution profile desired.

The new salts according to the present invention can also be used locally on the skin, or mucous membranes formulated as creams, lotions, ointments, or gels. As an example, doxycyclin sucrose octasulphate is well suited for insertion in or around the periodontal pocket of an individual sufferent from periodontitis. In this case, the vehicle described in U.S. Pat. No. 5,143,934 (Dumex) is especially advantageous to use as a carrier.

The bioadhesion properties of the drug:sugar acid salts of the invention may be tested in vitro on the test systems described below with reference to FIGS. 2 and 3 of the accompanying drawings.

1. In vitro Test System for Bioadhesion by means of Rabbit Jejunum Membranes

The bioadhesive test system described in the following is a modified system of a method described by Ranga Rao and Buri, 1989.

Male albino rabbits (3–4 kg) (New Zealand white rabbit SSC:CPH) where fasted for 20 hours before they were killed by means of a pentobarbital sodium injection. The intestines of the rabbits were dissected, and placed in an isotonic 0.9% sodium chloride solution at ambient temperature (about 18° C.). Within 30 minutes the jejunums were cut and washed with 0.9% sodium chloride solution. The lumens were gently rinsed with the saline until the intestines were clean. The jejunums were cut into pieces of 8–9 cm and immediately frozen (−20° C.). The intestines were stored up to 3 months before use. Before testing, the segment of jejunum was gently thawed out.

The segment of jejunum was cut longitudinally. It was placed on a stainless steel support (a tube of 2 cm in diameter and cut longitudinally at its centre) with the mucosa layer facing up, spread and held in position on the support by the adhesive effect of the jejunum itself. The support with the jejunum was placed at an angle of −7 to −21° in a cylindrical cell thermostated at 37° C. A schematic description of the cell is shown in FIG. 2. The relative humidity in the thermostatic cell was kept at 100%. The intestines were then flushed with isotonic 0.02 M phosphate buffer solution (pH 6.5, 37° C.) for 5 minutes at a flow rate of 10 ml min$^{-1}$; using a peristaltic pump, to equilibrate the intestine with the buffer and to rinse off loose mucosa. An accurately weighed amount of the sample to be tested for bioadhesiveness (about 50–150 mg) was placed evenly on the mucosa of the jejunum (0.8×6 cm). About 1 ml of the buffer solution was carefully dropped evenly onto the sample to ensure hydration. Immediately after, the segments were left for 10 minutes in the cell allowing the sample to interact with the glycoproteins of the jejunum and to prevent drying of the mucus. After 10 minutes the segments were evenly flushed with the isotonic 0.02 M phosphate buffer solution (pH 6.5, 37° C.) for 30 minutes at a constant flow rate of 5–15 ml min$^{-1}$. The tip of the tube carrying the buffer solution was placed 3–4 mm above the jejunum to ensure an even liquid flow over the mucosa. The effluent was collected into a beaker. The amount of bioadhesive component remaining on the jejunum was calculated either by measuring the amount of compound remaining on the jejunum or by measuring the amount in the receiver by means of HPLC. Other tissue than rabbit jejunum may be applied. Eg. buccal mucosa, stomach, intestine obtained from eg. pig, rat and rabbit.

2. In vitro Test System for Bioadhesion by means of Tensiometry

The test system for bioadhesion described in the following is a modified system of a method described by Tobyn, Johnson and Gibson (in "Use of a TA.XT2 Texture Analyser in Mucoadhesive Research", International LABMATE, 1992, XVII (issue VI), 35–38).

The test system involves measuring the tensile force required to break an adhesive bond formed between a model membrane and a test sample (i.e the sample which is tested for its bioadhesive properties).

Figure 3:
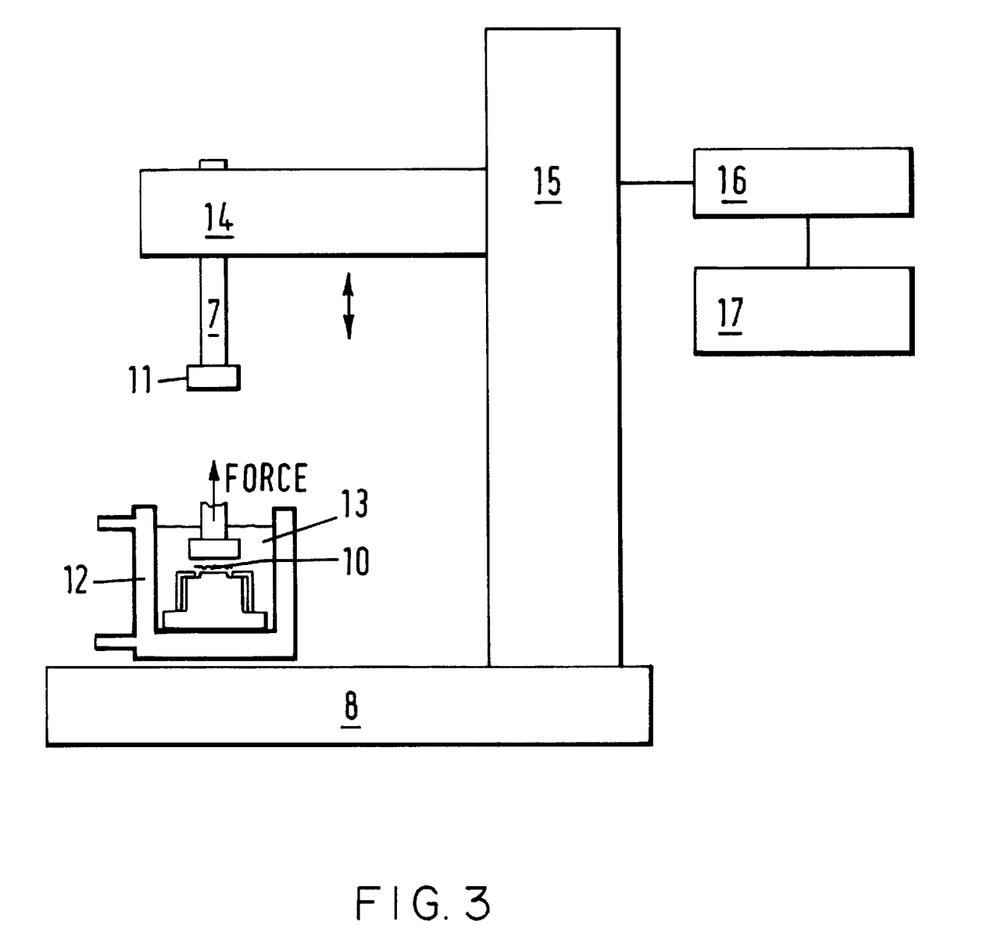
FIG. 3 is a schematic representation of apparatus which may be used to evaluate bioadhesion by tensiometry.

The test apparatus employed in the following is a TA.XT2 Texture analyser (Stable Micro System Ltd., Haslemere, UK) (FIG. 3). The test enables measuring the strength of adhesive bonding established by contacting a model membrane, i.e. in this case a rabbit intesting segment, and the test sample. An analogous test apparatus may also be employed.

The TA.XT2 Texture analyser apparatus is equipped with an instrument probe 7 (see FIG. 3) on a sliding stand 14 which is movable in a vertical direction at a variable rate under the control of a motor and displacement transducer 15 operated by control unit 17 and computer 17. During the so-called withdrawal phase of the testing, the instrument probe is moved upwards with a constant rate until detachment occurs (see below). Furthermore, the apparatus is equipped with a stationary place 8 on which a first holder 9 is placed. Before and during a test run, a model membrane 10 is fixed on this holder, e.g. by means of a cap or double adhesive tape or glue. The holder is constructed so that a well-defined area of the model membrane (about 0.5–9 cm$^2$) is used in the test runs. The accurate size of the exposed area is used in the calculation of the adhesive strength (see below).

As mentioned above, the test involves employment of a model membrane, primarily of animal origin. The membrane could be e.g. rabbit, rat or pig gastric mucosa; a segment of rabbit, rat or pig intestines, e.g. a segment of rabbit jejunum; or a segment of rabbit, rat or pig intestines from which the mucosal layer has been removed prior to testing; or skin from an animal (after removal of substantially all subcutaneous fat); or it could be artificial or commercial available mucin.

In the test described below, a model membrane of a segment of rabbit intestines, i.e. a segment of rabbit jejunum has been employed. However, it is appreciated that a change of membrane in some case may be advantageous, e.g. if a relatively large surface area of a model membrane is required. If the results obtained by use of another membrane than the rabbit intestine model membrane are used to compare the bioadhesive properties of various substances or combinations, the results of a reference compound could be included. As discussed below testing of a reference sample may also be made as a routine. Polycarbophil and Carbopol 934 have been found suitable as reference compounds.

A test sample (about 50–500 mg) is applied in a uniform layer either i) on the luminal side of the model membrane 10 placed on the first holder 9, or ii) directly on the instrument probe 7, if necessaty by means of a double adhesive tape or glue applied on the instrument probe before application of the test sample.

In those cases where it is not possible to fix the test sample to the instrument probe, the apparatus may be equipped with a second holder 11 on which another model membrane is fixed. In such cases, the model membranes employed on the two holders are usually of the same type (e.g. segments of rabbit jejunum). It is also possible to fix the other model membrane directly to the instrument probe e.g. by means of a duple adhesive tape or glue.

Test runs are usually performed in an aqueous medium and the temperature is maintained at 37° C. by use of a thermostatically controlled heater/stirrer 12. The aqueous medium is contained in a vessel 13. Prior to testing, the model membrane and the test sample is allowed to equilibrate with the aqueous medium for about 5–30 minutes. The aqueous medium is usually added during or after the initial test phase in which the two substrates (i.e. the model membrane and the test sample) are gently contacted with each other by means of lowering the instrument probe. As aqueous medium is used isotonic 0.02 M phosphate buffer solution, pH 6.5 but it may be replaced by other aqueous solutions.

In some cases it is desirable to avoid testing in an aqueous medium (e.g. in those case where the test sample has a relatively low dynamic viscosity); however, in order to avoid drying of the model membrane, a solvent evaporation trap may be employed, whereby the temperature (about 37° C.) and the humidity (at least about 80%) are controlled during testing. In those cases where the test sample can form a fluid crystalline phase, it may also be necessary to add a sufficient amount of water in order to induce formation of such a fluid crystalline phase.

Test runs are performed as follows:

The instrument probe (either with or without a second holder 11) is lowered in order to bring the model membrane and the test sample in contact under a constant force (preload of 0.05–2 N). After a time period of about 30 sec–3 minutes of contact time, the withdrawal phase is initiated by applying a vertically acting force by raising the instrument probe at a constant speed of about 0.1–0.2 mm sec$^{-1}$ until the two substrates (i.e. the model membrane as a first substrate and the test sample as a second substrate) are completely detached. The force required for detachment is recorded. Data is continuously collected and calculations are performed by means of a software program "XTRA Dimension software package" available from Stable Micro Systems, UK. The maximum force of detachment represents the adhesion strength (N cm$^{-2}$) and the area under the force/time (or force/distance) curve is considered as the adhesion work (mJ).

Determination of the Bioadhesive Properties of a Test Sample

In order to test whether a test sample is bioadhesive, two test runs are performed:

1. A test run without any test sample applied (result: adhesion strength $T_0$)

2. A test run with the test sample applied (result: adhesion strength T).

In both cases the adhesion strength is calculated and the test sample is considered bioadhesive if $T/T_0 \times 100\%$ is at least 115%, such as 125%, 135%, 150%, 175%, 200%.

Alternatively, a test run with the test sample is performed and the results are compared with the results of testing known bioadhesive substances such as, e.g. polycarbophil (a strong bioadhesive substance), or chitosan, tragacanth, hydroxypropylmethylcellulose (HPMC), hydroxypropylcellulose (HPC), karaya gum, carboxymethylcellulose (CMC), gelatin, pectin, acacia, PEG 6000, povidone, or DEAE-dextran (less bioadhesive than polycarbophil).

Polycarbophil (Noveon™ AA-1, BF Goodrich, Hounslow, U.K.) is a high molecular weight poly(acrylic acid) copolymer loosely cross-linked with divinyl glycol. On account of its known excellent mucoadhesive properties, this polymer serves as a reference. Before testing in the above-mentioned tensiometric test, a polycarbophil gel is prepared by mixing polycarbophil with water (resulting concentration about 10–20 mg ml$^{-1}$) and the mixture is allowed to hydrate at 37° C. for 24 hours. The polymer solution is periodically stirred. The pH is adjusted to 5.1 using either diluted sodium hydroxide or hydrochloric acid. The resulting gel is tested as described above and the result obtained is used as a reference value for excellent bioadhesive substances. Similarly, other substances which are known bioadhesive substances are tested, and by choosing test substances with various degrees of bioadhesiveness so that an evaluation scale can be made, the performance of a test sample with respect to bioadhesiveness can be evaluated. It is contemplated that the following scale is applicable (force resolution 0.1 gm):

| Bioadhesive properties | Adhesion force (mN cm$^{-2}$) |
| --- | --- |
| none | less than 0.1 mN cm$^{-2}$ |
| poor | about 0.1–about 1 mN cm$^{-2}$ |
| moderate | about 1–about 4 mN cm$^{-2}$ |
| good | about 4–about 10 mN cm$^{-2}$ |
| excellent | more than 10 mN cm$^{-2}$ |

In some cases, e.g. in the case of tablets with excellent bioadhesive properties, an adhesion force may be as high as about 700 mN cm$^{-2}$ or even higher.

3. In vitro Test System for Bioadhesion by means of Tensiometry—Determination of Duration of Adhesion The test system described in the following is a modified system of a method described by Smart (Int. J Pharm. 73:69–74(1991)).

The apparatus and conditions employed in this test are the same as described in the test denoted 2 above.

The duration of adhesion is evaluated by applying a constant tensile force between about 0.25–2 N cm$^{-2}$, such as 1 N cm$^{-2}$, to the adhesion bond after the initial contact time (see above: 0.5–3 minutes) and leaving for up to 8 hours or until the bond fractures. Every hour the tensile force acting on the adhesive joint is noted and if necessary adjusted to the initial value (eg. 1 N cm$^{-2}$). After 8 hours the force required to break the adhesive bond is evaluated.

All publications referred to hereinbefore are incorporated herein by reference.

The invention will now be described by reference to the following non-limiting Examples.

EXAMPLE 1

Sucrose-octa-O-sulphonic Acid 60 g (50 mmol) of sucrose-octa-O-sulphonic acid sodium salt (produced in accordance with J. Chem. Soc. Faraday Trans., 1981, 77, pages 629–639) are dissolved in 200 ml of water and cation exchanged on Amberlite® IR (H$^+$). The combined eluates are diluted to 1 liter corresponding to an 0.05 M solution.

EXAMPLE 2

Doxycyclin Sucrose-octa-O-sulphonic Acid Salt 18.5 g (40 mmol) doxycyclin monohydrate is dissolved in 400 ml 0.1 M HCl and by addition of 6.5 g (5 mmol), sucrose-octa-O-sulphonic acid-Na$_8$, 8 aq., dissolved in 300 ml water, precipitation of doxycyclin sucrose octasulphate takes place. The reaction mixture is stirred for about 60 min at 25° C., filtered, washed with 3×50 ml water by dispersion and refiltration and vacuum dried at about 1 Torr/25° C./sicapent®/20 h.

Yield: 23.5 g.

MP.: 150° C. (decomp.).

Stoichiometric proportions: in the batches produced, the content of water was found to be about 10%. The content of doxycyclin was found to be about 77%, calculated with reference to the dried substance. This content of doxycylin indicates that 8 moles of doxycyclin complex with 1 mole of sucrose-octa-O-sulphonic acid.

EXAMPLE 3

Doxycyclin SOS Salt 20.5 g doxycylin hyclate (40 mmol) is dissolved in 400 ml water and with vigorous stirring, 100 ml of the acid solution of Example 1 is added. After 30 min, the pH is adjusted to 3.5 with 0.1 M NaOH solution. After another 30 min of stirring, the precipitate is filtered and dried as in Example 2.

EXAMPLE 4

Doxycyclin SOS Salt 18.5 g (40 mmol) doxycyclin monohydrate is dissolved in 400 ml 0.1 M HCl and by titration with 100 ml 0.05 M (5 mmol) sucrose-octa-O-sulphonic acid, precipitation of doxycyclin sucrose octa sulphate takes place. The reaction mixture is stirred for about 60 min at 25° C., filtered, washed with 3×50 ml water (by dispersion and refiltration) and vacuum dried at about 1 Torr/25° C./sicapent®/20 h.

EXAMPLE 5

Doxycyclin SOS Salt

By titration of 6.5 g (5 mmol) sucrose-octa-O-sulphonic acid Na$_8$, 8 aq. dissolved in 300 ml water, with 18.5 g (40 mmol) doxycylin monohydrate dissolved in 400 ml 0.1 M HCl, precipitation of doxycycline sucrose octasulphate takes place. The reaction mixture is stirred for about 60 min at 25° C., filtered, washed with 3×50 ml water (by dispersion and refiltration) and vacuum dried at about 1 Torr/25° C./sicapent®/20 h.

EXAMPLE 6

Dissolution of Doxycyclin Sucrose Octasulphate

The paddle method is used in accordance with USP XXII, p. 1579, (apparatus II), with 900 ml 0.1 N HCl. One tablet containing 150 mg doxycyclin sucrose octasulphate (equal to 105 mg doxycyclin) is placed in the dissolution apparatus. Samples are taken after 5, 10, 20, 30 and 60 minutes and diluted.

The samples are analyzed spectrophotometrically at 345.9 nm in a Shimadzu 160 A photometer.

The results are compared to samples of Vibramycin® from Pfizer, which contains doxycyclin carragenate.

Figure 1:
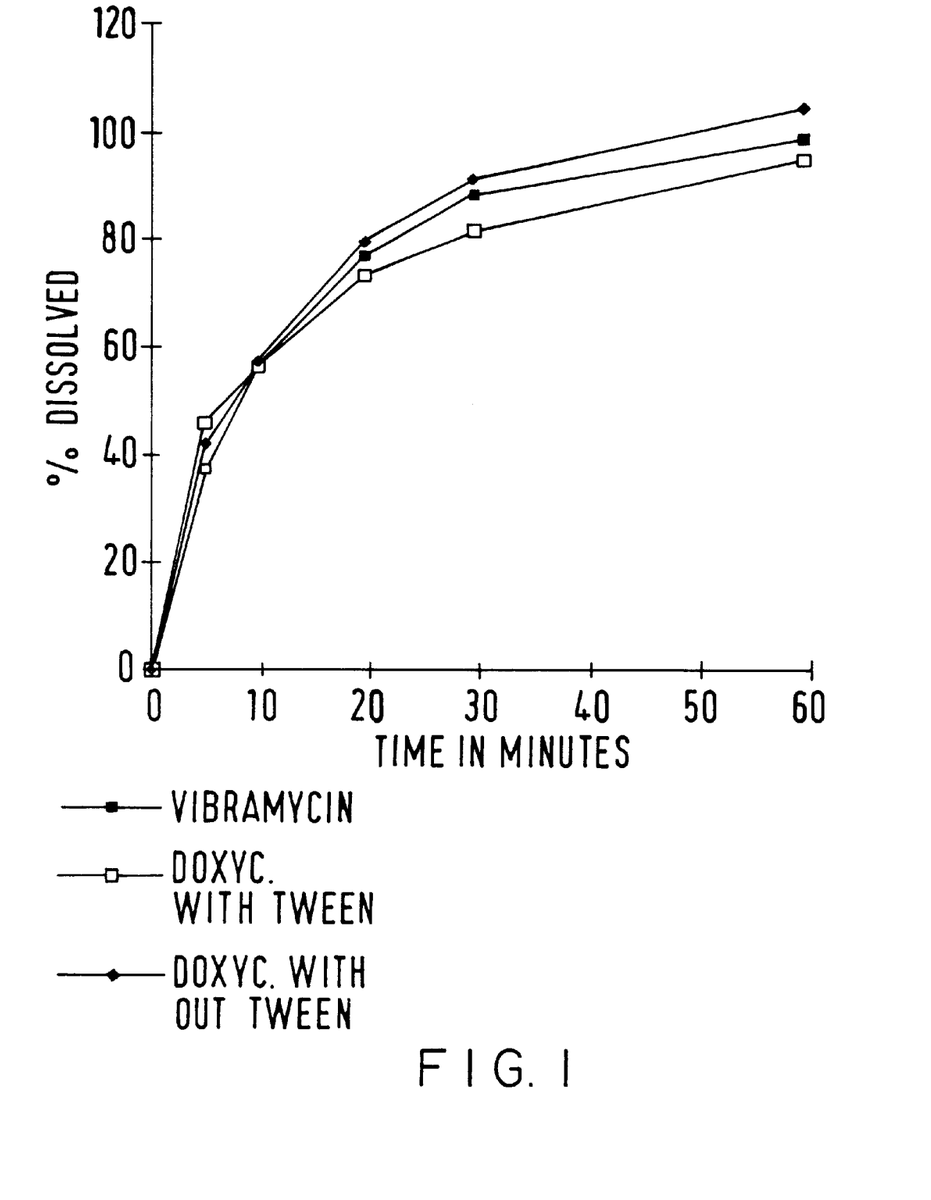
FIG. 1 is a plot of dissolution rate for doxycyclin.SOS salt according to the invention compared with the commercial product Vibramycin.

In FIG. 1, the plot of release versus time is illustrated graphically. This shows that the delayed release characteristics are similar despite the major differences in the counterion.

EXAMPLE 7

Kanamycin A Salt of Sucrose-octa-O-sulfonic Acid 17 g (25 mmol) of kanamycin A sulfate (Maiji Seika Kaisha Ltd., Tokyo, JP) is dissolved in 100 ml of ion exchanged water. The solution is eluted through an anionic ex-changer, Amberlyst A26® (OH⁻). The combined eluates are evaporated on a rotary evaporator to 100 ml and are titrated with an 0.05M solution of sucrose-octa-O-sulfonic acid (from Example 1) to a pH of 5.0. The product precipitates as a syrup. The supernatant is decanted. To the syrup is added 250 ml of EtOH and stirring is effected for 3 hours thereby effecting crystal precipitation.

The crystals are filtered off, washed with 2×25 ml of EtOH and vacuum dried over Sicapent at 45° C.

Yield: 20 g (about 82%).

By DSC (Differential Scanning Calorimetry) the substance pyrolyses within the interval ranging from 180 to 195° C. and exhibits no melting point.

HPLC shows that the stoichiometric composition is a kanamycin:sucrose-octa-O-sulfonic acid ratio of 2:1.

EXAMPLE 8

Small-scale Dissolution Test 250 mg of kanamycin salt of sucrose-octa-O-sulfonic acid in 25 ml of ion-exchanged water, 5% $NaH_2PO_4$ buffer pH 4.3 and 0.01 M HCl, respectively at 37±0.5° C. show that the substance has low solubility in water and only dissolves by ion exchange. The solubility is thus proportional with the ion activity.

EXAMPLE 9

Gentamycin Salt of Sucrose-octa-O-sulfonic Acid 735 mg (1 mmol) of Gentamycin sulfate (Sigma, G-3632, 648 μg/mg) is dissolved in 25 ml of ion exchanged water. The solution is eluted through an anion exchanger as in Example 7. The combined basic eluates are titrated with an 0.05 M solution of sucrose-octa-O-sulfonic acid (from Example 1) to a pH of 6.5. The solution is evaporated to about 5 ml which is triturated with 75 ml of ethanol. Stirring is maintained for three hours which results in crystal precipitation.

The crystals are filtered off, washed with 2×10 ml of EtOH and vacuum dried over Sicapent at 45° C.

Yield 950 mg (about 98%).

DSC shows that the substance pyrolyses in the interval of 210–215° C. and shows no melting point.

EXAMPLE 10

Neomycin Salt of Sucrose-octa-O-sulfonic Acid 910 mg (1 mmol) of neomycin sulfate (Sigma, N-1876, 657 μg/mg) is dissolved in 25 ml of ion exchanged water. The solution is eluted through an anion exchanger, as in Example 7. The combined eluates are titrated with an 0.05M solution of sucrose-octa-O-sulfonic acid (from Example 1) to a pH of 6.5. The solution is evaporated to about 5 ml which is triturated with 75 ml of EtOH. Stirring is maintained for three hours which leads to crystal precipitation.

The crystals are filtered off, washed with 2×10 ml of EtOH and vacuum dried over Sicapent at 45° C.

Yield: 1 g (about 90%).

DSC shows that the substance pryolyses in the interval of 190–210° C. and shows no melting point.

EXAMPLE 11

Streptomycin Salt of Sucrose-octa-O-sulfonic Acid 1550 mg (1 mmol) of streptomycin sulfate (Sigman, S-6501, 766 units/mg) is dissolved in 25 ml of ion exchanged water. The solution is eluted through an anion exchanger, as in Example 7. The recovered eluates are titrated with an 0.05M solution of sucrose-octa-O-sulfonic acid (from Example 1) to a pH of 6.5. The solution is evaporated to about 5 ml and is triturated with 75 ml of EtOH. Stirring is maintained for three hours which leads to crystal precipitation.

The crystals are filtered off, washed with 2×10 ml of EtOH and vacuum dried over Sicapent at 45° C.

Yield: 1.5 g (about 91%).

DSC shows that the substance pyrolyses in the interval of 200–210° C. and shows no melting point.

EXAMPLE 12

Tobramycin Salt of Sucrose-octa-O-sulfonic Acid 500 mg (1 mmol of tobramycin base (Sigma, T-4014, 941 μg/mg) are dissolved in 25 ml of ion exchange water titrated with an 0.05 M solution of sucrose-octa-O-sulphonic acid (from Example 1) to a pH of approximately 6.5.

The emulsion thus formed is evaporated to about 5 ml and is triturated with 75 ml of ethanol. Stirring is maintained for three hours which results in crystal precipitation. The crystals are filtered off, washed with 2×5 ml of ethanol and vacuum dried over Sicapent at 45° C.

Yield: 650 mg (about 68%).

DSC shows that the substance pyrolyses in the interval 215–230° C. and shows no melting point.

HPLC shows that stoichiometric composition is a tobramycin:sucrose-octa-O-sulphonic acid ratio of 1.6:1.

EXAMPLE 13

Kanamycin/aluminium Salt of Sucrose-octa-O-sulphonic Acid

The mixed salt is produced by admixing amounts of sucrose-octa-O-sulphonic acid with kanamycin A base with the pH subsequently being adjusted to 5.2 with a slurry of $Al(OH)_3$ in water. The resulting gel is evaporated in a rotation evaporator to form an amorphous powder.

The production of corresponding salts with NaOH, $Ca(OH)_2$ and $Mg(OH)_2$ is carried out analogously.

EXAMPLE 14

The reaction of the compounds of Examples 7 and 9 to 13 with water is a swelling reaction whereby a sticky substance or syrup is formed. The absorption of water occurs to a certain point where the particles have become an oily, viscous fluid which has comparatively low solubility in water. When a drop of this fluid is applied to smooth skin, a membrane is formed which has low solubility in water and which may only be removed by intensive scrubbing with water. By rinsing with ion-containing water, the membrane is gradually dissolved until it disappears completely.

EXAMPLE 15

Production of Kanamycin Salt of Sucrose-octa-O-sulphonic Acid using Na-sucrose-octa-O-sulphate as a Starting Material 7.75 g (10 mmol) of kanamycin A-sulphate dissolved in 50 ml of water is admixed with 6.5 g (5 mmol) of sodium sucrose-octa-sulphate, $C_{12}H_{14}S_8O_{35}Na_8$, $8H_2O$, produced in accordance with Example 1.

The mixture is dialysed until the ion strength of the washing water is constant, at this point kanamycin-octasulphate is dissolved, and the solution becomes milky.

The emulsion is evaporated to about 25 ml and triturated with 250 ml of etanol whereby crystallisation occurs. Stirring is maintained for 3 hours and crystals are filtered off and dried as in Example 7.

Yield: 9.55 g (about 98%).

Analysis of the product gives the same results as for Example 7.

EXAMPLE 16

Sucrose-octa-O-sulphonic Acid-Al-tobramycin 5.6% Salt (a) 5 mmol sucrose-octa-O-sulphonic-acid-tobramycin$_{1.6}$ (prepared in Example 12) and 7 mmol Na-sucrose-octa-O-sulphate is dissolved in 150 ml water.

(b) 112 mmol $AlCl_3$ in 100 ml water is mixed with 224 mmol NaOH in 100 ml water.

Solutions (a) and (b) are mixed with stirring. The pH is adjusted to and maintained at 5.5 with 0.25M NaOH, whereby a precipitate is formed. The precipitate is filtered off, washed with 4×25 ml of water and dried in vacuum oven at 25° C./$P_4O_{10}$.

Yield 75%.

The content of tobramycin is shown by HPLC to be 5.6%.

EXAMPLE 17

Test for Bioadhesion on Mucosal Surfaces

Figure 2:
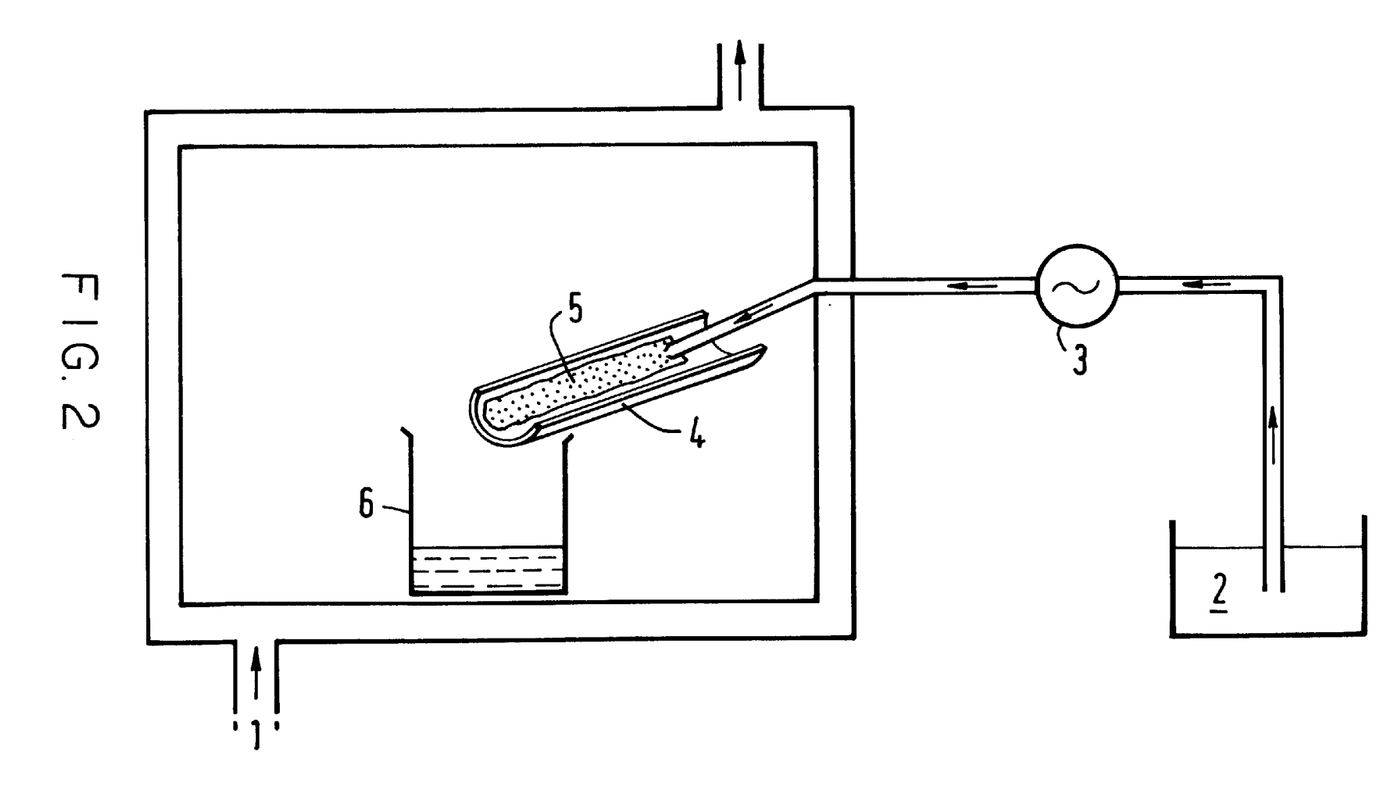
FIG. 2 is a schematic representation of apparatus used for the determination of drug retention on gastrointestinal mucous membrane.

The bioadhesion of the novel salts according to the invention is demonstrated in the test system shown in FIG. 2 wherein (1) is thermostatic water flow at 40° C., (2) is a reservoir containing the washing solution at 37° C., (3) is a peristaltic pump, (4) is a stainless steel support, (5) is a model membrane, and (6) is a receiver for collecting the washings.

A segment of jejunum from rabbit is placed on a support (4) with the mucosa facing upwards, spread and held in position on the support by the adhesive effect of the jejunum itself. Support and jejunum are placed at an angle of −7° C. in a cylindrical cell thermostated at 37° C. The sample to be tested is placed on the jejunum and 1 ml buffer is dropped thereon. The buffer used is either a 0.01 M HCl solution, pH 2 (buffer a) or borate buffer solution 0.05 M, pH 7.4 (buffer b). The segments are left for 10 minutes in the cell to allow the test substance to interact with the glycoproteins of the mucosa. After 10 minutes the jejunum is flushed with either buffer a or b for 30 minutes.

The buffer is collected in a receiver (6). The amount of test substance remaining on the jejunum is calculated by measuring the amount in the receiver by means of HPLC.

In a first experiment, the tobrymycin-SOS salt from Example 12 containing 44% tobramycin, was tested. As a reference, a physical mixture of sucralfate 56%/tobramycin 44% was used.

The following results were obtained:

| Test Substance | Buffer a. pH 2.0 | Buffer b. pH 7.4 |
|---|---|---|
| SOS-tobramycin salt from Example 12 | 59% | 31% |
| SOS/tobramycin physical mixture 56:44 | 8% | 1% |

The percentages indicate the amount of test substance remaining on the mucosa.

In a second experiment, the following results were obtained:

| Test Substance | Buffer a. pH 2.0 | Buffer b. pH 7.4 |
|---|---|---|
| SOS-Al-tobramycin salt from Example 16 | 61% | 65% |
| Sucralfate 94.4%-tobramycin 5.6% physical mixture | 40% | 50% |

The percentages indicates the amount of test substance remaining on the mucosa.

These experiments clearly demonstrate that the novel salts according to the invention are superior to simple physical mixtures of sucralfate and tobramycin.

EXAMPLE 18

Preparation of salts of sucrose-octa-O-sulphonic acid-tobramycin-Al

I: Preparation of Al(OH)$_3$Cl-reagent (I):

0.2 mol AlCl$_3$, 6 aq, ca. 48.2 g is dissolved in 200 ml demineralised water. The pH is adjusted to 3.5–4 with 0.4 mol NaOH (ca. 200 ml 2M NaOH). The solution is metastable and is kept at +5° C.

II: Preparation of Al(OH)$_3$Cl reagent (II):

0.2 mol AlCl$_3$, 6 ca. 48.2 g is dissolved in 300 ml demineralised water and the pH is adjusted to 3.9 with a strong basic ion exchange reagent, eg. Amberlite® A-26 in hydroxide-form. The adjustment is done over 5 minutes with moderate stirring. The anion exchange reagent is filtered off and eluted with 200 ml of water for 30 minutes. The combined filtrate and eluate are filtered through celite.

The solution is metastable and is kept at +5° C.

III: 100 ml, 0.1 M (ca 10 mmol) SOSH$_8$, prepared in Example 1 is mixed with 8.5 g tobramycin base, dissolved in 50 ml water. The mixture is stirred for 10 minutes and 400 ml of 0.5 M Al (OH)$_2$-reagent (I) is added (ca 200 mmol Al(OH)$_2$$^+$). Stirring is continued for 10 minutes, 100 ml 2 M NaOH (ca 200 mmol) is added which results in the formation of a precipitate. Stirring is continued for 2 minutes and the crystals are filtered off on a glass filter, washed with 50 ml water, and dried in vacuum over at 80° C./1 Torr/20 hours.

Yield: ca 35 g (73%).

IV:

Same procedure as III, but using reagent II in place of reagent I.

Yield: 36 g (about 75%).

EXAMPLE 19

Diltiazem Salt of Sucrose-octa-O-sulphonic Acid 16.7109 g (37.0546 mmol) Diltiazem.Hcl is dissolved in 400 ml ion-exchanged water (pH 4.42) and by addition of 6.5281 g (5.6344 mmol) sucrose-octa-O-sulphonic acid-$Na_8$, 8 aq., dissolved in 200 ml ion-exchanged water, precipitation takes place. The reaction mixture is filtered and vacuum dried at ca. 1 Torr/25° C./20 h/Sicapent®.

Yield: 19.1166 g

DSC showed decomposition from about 170° C.

Water content: 3.9%

EXAMPLE 20

Cyclobenzaprine Salt of Sucrose-octa-O-sulphonic Acid

Analogously to Example 19, using 12.4763 g (40.0087 mmol) Cyclobenzaprine.HCl in 400 ml ion-exchanged water (pH 4.15) and 5.8159 g (5.0198 mmol) sucrose-octa-O-sulphonic acid-$Na_8$, 8 aq., in 300 ml ion-exchanged water.

Yield: 4.5709 g

DSC showed decomposition from about 200° C.

EXAMPLE 21

Noscapine Salt of Sucrose-octa-O-sulphonic Acid

Analogously to Example 19, using 17.9965 g (40.0020 mmol) Noscapine.HCl in 400 ml ion-exchanged water (pH 3.86) and 5.7910 g (4.9983 mmol) sucrose-octa-O-sulphonic acid-$Na_8$, 8 aq., in 300 ml ion-exchanged water.

Yield: 17.0296 g

DSC showed decomposition from about 200° C.

EXAMPLE 22

Erythromycin Salt of Sucrose-octa-O-sulphonic Acid 9.9861 g (6.8941 mmol) Erythromycin Lactobionate is dissolved in 400 ml ion-exchanged water (pH 6.74). The solution is adjusted to pH about 4.00 with 1M HCl (pH 4.33). A solution of 1.0021 g (0.8649 mmol) sucrose-octa-O-sulphonic acid-$Na_8$, 8 aq., in 300 ml ion-exchanged water is added, which results in precipitation. The reaction mixture is filtered and vacuum dried at about 1 Torr/25° C.,/20 h/Sicapent®.

Yield: 3.8896 g

DSC showed decomposition from about 200° C.

EXAMPLE 23

Imipramine Salt of Sucrose-octa-O-sulphonic Acid

Analogously to Example 22, using 3.9789 g (12.5573 mmol) Imipramine.HCl in 200 ml ion-exchanged water (pH 5.46) and 1.8809 g (1.6234 mmol) sucrose-octa-O-sulphonic acid-$Na_8$, 8 aq., in 100 ml ion-exchanged water.

Yield: 0.7618 g

EXAMPLE 24

Nortriptyline Salt of Sucrose-octa-O-sulphonic Acid

Analogously to Example 22, using 0.7358 g (2.4540 mmol) Nortriptyline.HCl in 100 ml ion-exchanged water (pH 6.22) and 0.3647 g (0.3148 mmol) sucrose-octa-O-sulphonic acid-$Na_8$, 8 aq., in 100 ml ion-exchanged water.

Yield: 0.7844 g DSC showed decomposition from about 190° C.

EXAMPLE 25

Ouinidine Salt of Sucrose-octa-O-sulphonic Acid

Analogously to Example 22, using 3.8360 g (5.1357 mmol) Quinidine Sulphate in 400 ml ion-exchanged water (pH 6.29) and 0.7505 g (0.6478 mmol) sucrose-octa-O-sulphonic acid-$Na_8$, 8 aq., in 100 ml ion-exchanged water.

Yield: 1.4638 g

DSC showed decomposition from about 175° C.

EXAMPLE 26

Benztropine Salt of Sucrose-octa-O-sulphonic Acid

Analogously to Example 22, using 4.0353 g (9.5739 mmol) Benztropine Mesylate in 300 ml ion-exchanged water (pH 6.23) and 1.4011 g (1.2093 mmol) sucrose-octa-O-sulphonic acid-$Na_8$, 8 aq., in 150 ml ion-exchanged water.

Yield: 3.0020 g

EXAMPLE 27

Verapamil Salt of Sucrose-octa-O-Sulphonic Acid

Analogously to Example 22, using 0.7512 g (1.5298 mmol) Verapamil.HCl in 200 ml ion-exchanged water (pH 6.17) and 0.2226 g (0.1921 mmol) sucrose-octa-O-sulphonic acid-$Na_8$, 8 aq., in 100 ml ion-exchanged water.

Yield: 0.2791 g

EXAMPLE 28

Bacitracin Salt of Sucrose-octa-O-sulphonic Acid 11.8176 g (8.3074 mmol) Bacitracin is dissolved in 400 ml 0.1M HCl (pH 2.16) and by addition of 5.7098 g (4.9282 mmol) sucrose-octa-O-sulphonic acid-$Na_8$, 8 aq., dissolved in 300 ml ion-exchanged water, precipitation takes place. The reaction mixture is filtered and vacuum dried at 1 Torr/25° C./20 h/Sicapent®.

Yield: 7.5705 g

DSC showed decomposition from about 150° C.

EXAMPLE 29

Polymyxin Salt of Sucrose-octa-O-sulphonic Acid

Anlogously to Example 28, using 10.0453 g (8.3711 mmol) Polymyxin in 400 ml 0.1M HCl (pH 1.60) and 1.2384 g (1.0689 mmol) sucrose-octa-O-sulphonic acid-$Na_8$, 8 aq., in 200 ml ion-exchanged water.

Yield: 4.3644 g

DSC showed decomposition from about 160° C.

EXAMPLE 30

Vancomycin Salt of Sucrose-octa-O-sulphonic Acid

Analogously to Example 28, using 7.6646 g (5.2888 mmol) Vancomycin in 200 ml 0.1M HCl (pH 1.58) and 0.8011 g (0.6914 mmol) sucrose-octa-O-sulphonic acid-$Na_8$, 8 aq., in 100 ml ion-exchanged water.

Yield: 2.8677 g

DSC showed decomposition from about 135° C.

EXAMPLE 31

Flunarizine Salt of Sucrose-octa-O-sulphonic Acid

Analogously to Example 28, using 0.7635 g (1.5992 mmol) Flunarizine.2HCl in 200 ml 0.1M HCl (pH 1.31) and 0.2414 g (0.2084 mmol) sucrose-octa-O-sulphonic acid-$Na_8$, 8 aq., in 100 ml ion-exchanged water.

Yield: 0.6669 g

EXAMPLE 32

Ergotamine Salt of Sucrose-octa-O-sulphonic Acid 1.0189 g (0.7758 mmol) Ergotamine Tartrate is dissolved in 400 ml 0.1M HCl (pH1.62). The compound is almost insoluble, so the solution has to be decanted. A solution of 0.1302 g (0.1124 mmol) sucrose-octa-O-sulphonic acid-$Na_8$, 8 aq., in 100 ml ion-exchanged water is added, which results in precipitation. The reaction mixture is filtered and vacuum dried at about 1 Torr/25° C./20 h/Sicapent®.

Yield: 0.5549 g

EXAMPLES 33 to 45

Formation of Aqueous Sparingly Soluble Dextran-Drug Complexes

The experiments were carried out in aqueous solutions, and the precipitations were generally performed at pH 4–6.

Three different derivatives of dextran were used: dextran phosphate ($M_{wt}$=72000, P:14%); dextran sulphate ($M_{wt}$= 12000, S:17%); dextran sulphate ($M_{wt}$=120000, S:14.2%). The derivatives were obtained from Pharmacia, Biotech, Sweden.

To obtain a complete binding of drug to all sulphur/phosphorus oxyacid-groups on the dextran molecule, the amount of drug added to the dextran solution had to be at least equimolar to the amount of sulphur/phosphor bound to the dextran molecules. The desired concentration of dextran in the final mixed solution was 10 g/l for dextran phosphate and 5 g/l for the dextran sulphates.

For i.e dextran phosphate ($M_{wt}$=72000, P: 14%), the following equation was used:

Final volume of solution: 6 ml.–60 mg dextran phosphate 60 mg dextran phosphate=60*0.14 mg phosphate=8.4 mg phosphate =0.0084/30.97 mol phosphate=$2.7*10^{-4}$ mol phosphate Amount drug to be added: $2.7*10^{-4}*M_{wt\ (drug)}$ g Similar calculations were made for the two dextran sulphates.

Procedure for precipitation of drugs with dextran phosphate and results:

A standard-solution of Dextran phosphate (20 g/l) was prepared.

The calculated amount of drug was dissolved in 3 ml of distilled water. In case of sparingly soluble drugs, pH was adjusted to 1–3 with 2 M HCl, to get the basic drugs on salt-form. Then 3 ml of the dextran solution was added. If no precipitation was observed, the pH of the solution was varied between 1–8 to see if the complex-formation/precipitation was pH-dependent.

The precipitate was separated, either by filtration through G3 glassfilters, or if the complex was very fine, by centrifugation and subsequent decantation of the solvent.

To confirm the dextran-drug complex formation, DSC analyses were performed.

Experimental results of complex formation with dextran phosphate ($M_{wt}$=72000, P: 14%):

| Drug | Precipitation | Example No. | DSC |
|---|---|---|---|
| Cyclobenzaprine ($M_{wt}$ = 257.4) | yes | 33 | confirmed |
| Polymyxin ($M_{wt}$ = 1202) | yes | 34 | |
| Imipramine ($M_{wt}$ = 315.4) | yes | 35 | — |

Procedure for precipitation of dextran sulphates and results:

A standard-solution of dextran sulphate (10 g/l) was prepared.

The calculated amount of drug was dissolved in 10 ml of distilled water. In case of sparingly soluble drugs, pH was adjusted to 1–3 with 1 M HCl, to get the basic drugs on salt-form. Then 10 ml of the dextran solution was added. If no precipitation was observed and the pH was different from 4–5, the pH of the solution was adjusted to this value.

The precipitate was separated, by centrifugation and subsequent decantation of the solvent.

To confirm the dextran-drug complex formation, DSC analyses were performed.

Experimental result of complex-formation with dextran sulphate ($M_{wt}$=120000, S: 14,2%

| Drug | Precipitation | Example No. | DSC |
|---|---|---|---|
| Cyclobenzaprine ($M_{wt}$ = 257.4) | yes | 36 | |
| Bacitracin ($M_{wt}$ = 1421) | yes | 37 | Confirmed |
| Polymyxin ($M_{wt}$ = 1202) | yes | 38 | |
| Vancomycin ($M_{wt}$ = 1449) | yes | 39 | — |
| Imipramine ($M_{wt}$ = 315.4) | yes | 40 | |
| Quinidine ($M_{wt}$ = 324.4) | yes | 41 | Confirmed |
| Ergotamine ($M_{wt}$ = 581.7) | yes | 42 | |

Experimental results of complex formation with dextran sulphate ($M_{wt}$=12000, S: 17%):

| Drug | Precipitation | Example No. | DSC |
|---|---|---|---|
| Cyclobenzaprine ($M_{wt}$ = 257.4) | yes | 43 | — |
| Polymyxin ($M_{wt}$ = 1202) | yes | 44 | Confirmed |
| Bacitracin ($M_{wt}$ = 1421) | yes | 45 | — |

EXAMPLE 46

Analysis of Sucrose-octa-O-sulphonic Acid Salts

The following drug substances and the Sucrose-octa-O-sulphonic acid salts of these substances were analysed as described below.

The Sucrose-octa-O-sulphonic acid salt of the active substance was dissolved in a 1% sodium chloride solution and analysed by HPLC, using the parameters below:

Mobile phase: Ammonium sulphate solution in water, 132 mg/ml.

Detection: Refractive index detector.

Column: 5% phenyl 95% methylpolysilane chemically bound to silica gel, 3.9 mm×30 cm.

The content of the active substances was measured by UV when possible, at a suitable $UV_{max}$ of the active substance.

The Sucrose-octa-O-sulphonic acid salt of the active substance was analysed by DSC. The melting point or destruction point of the active substance was determined. The destruction temperature of the Sucrose-octa-O-sulphonic acid salt of the substance was found, and it was shown that the melting or destruction temperature of the active substance could not be recognized in the Sucrose-octa-O-sulphonic acid salt. Additionally it was shown that the destruction temperature of Sucrose-octa-O-sulphonic acid sodium salt was different from the destruction temperature of the Sucrose-octa-O-sulphonic acid salt of the active substances.

Sucrose-octa-O-sulphonic acid sodium salt itself has a destruction temperature of about 125° C.

Bacitracin-SOS:

Bacitracin: Not analysed, due to no chromophoric groups being present.

DSC: The Sucrose-octa-O-sulphonic acid salt of bacitracin has no melting point, but starts to decompose at about 150° C. The destruction temperature of Sucrose-octa-O-sulphonic acid sodium salt is about 125° C., this indicates that Sucrose-octa-O-sulphonic acid and bacitracin precipitate as a salt.

Cyclobenzaprine-SOS:

Cyclobenzaprine: 32% calculated with reference to the non-dried substance.

DSC: Melting point of cyclobenzaprine was found to be 214.9° C.

The Sucrose-octa-O-sulphonic acid salt of cyclobenzaprine has no melting point, but the substance starts to decompose at about 200° C.

No endotherm was seen at 214.9° C., showing that cyclobenzaprine was not present as crystals in the mixture.

This indicates that Sucrose-octa-O-sulphonic acid and cyclobenzaprine precipitate as a salt.

Diltiazem-SOS:

Diltriazen: 79% calculated with reference to the non-dried substance.

DSC: Melting point of diltiazem was found to be 207.6° C.

The Sucrose-octa-O-sulphonic acid salt of diltiazem has no melting point, but the substance starts to decompose at about 170° C.

No endotherm was seen at 207.6° C., showing that diltiazem was not present as crystals in the mixture.

This indicates that Sucrose-octa-O-sulphonic acid and diltiazem precipitate as a salt.

Erythromycin-SOS:

Erythromycin: Not analysed, due to no chromophoric groups being present.

DSC: Erythromycin hydrated crystals melt at 135–140° C., resolidify and melt again at 190–193° C.

The Sucrose-octa-O-sulphonic acid salt of erythromycin has no melting point, but the substance starts to decompose at about 200° C.

A small exotherm and endotherm is seen at 130–140° C. showing that a small amount of erythromycin might be present as crystals in the salt. However, most of the erythromycin is not present as crystals in the mixture.

This indicates that Sucrose-octa-O-sulphonic acid and erythromycin precipitate as a salt.

Nortriptyline-SOS:

DSC: Melting point of nortriptyline was found to be 213.3° C.

The Sucrose-octa-O-sulphonic acid salt of nortriptyline has no melting point, but starts to decompose at about 190° C.

No endotherm was seen at 213.3° C., showing that nortriptyline was not present as crystals in the mixture.

This indicates that Sucrose-octa-O-sulphonic acid and nortriptyline precipitate as a salt.

Noscapine-SOS:

Noscapine: 87% calculated with reference to the non-dried substance.

DSC: Melting point of noscapine was found to be 203.7° C.

The Sucrose-octa-O-sulphonic acid salt of noscapine has no melting point, but starts to decompose at about 200° C.

No endotherm was seen at 203.7° C., showing that noscapine was not present as crystals in the mixture.

This indicates that Sucrose-octa-O-sulphonic acid and noscapine precipitate as a salt.

Polymyxin-SOS:

Polymyxin: Not analysed, due to an chromophoric groups being present.

DSC: Polymyxin starts to decompose at about 125° C.

The Sucrose-octa-O-sulphonic acid salt of polymyxin has no melting point, but does not start to decompose before about 160° C.

this indicates that polymyxin is not present as crystals in the mixture and that Sucrose-octa-O-sulphonic acid and polymyxin precipitate as a salt.

Quinidine-SOS:

DSC: Quinidine melts at about 170° C., recrystallizes and melts again at about 180° C.

The Sucrose-octa-O-sulphonic acid salt of quinidine has no melting point, but starts to decompose at about 175° C.

No endotherm was seen at 170 or 180° C., showing that quinidine was not present as crystals in the mixture. This indicates that Sucrose-octa-O-sulphonic acid and quinidine precipitate as a salt.

Vancomycin-SOS:

Vancomycin: Not analysed, due to no chromophoric groups being present.

DSC: Vancomycin starts to decompose at about 125° C.

The Sucrose-octa-O-sulphonic acid salt of vancomycin has no melting point, but does not start to decompose before about 135° C.

This indicates that vancomycin is not present as crystals in the mixture and that Sucrose-octa-O-sulphonic acid and vancomycin precipitate as a salt.

Verapamil-SOS:

Verapamil: 93% calculated with reference to the non-dried substance.

DSC: Melting point of verapamil was found to be 141.2° C.

The Sucrose-octa-O-sulphonic acid salt of verapamili has no melting point, but starts to decompose instead.

No endotherm was seen at 141.2° C., showing that verapamil was not present as crystals in the mixture.

This indicates that verapamil is not present as crystals in the mixture and that Sucrose-octa-O-sulphonic acid and verapamil precipitate as a salt.

EXAMPLE 47

Analysis of Dextran Phosphate Salts

The drug substance and the dextran phosphate salt of the substance were analysed as described below.

The dextran phosphate salt of the active substance was analysed by DSC. The melting point or destruction point of the active substance was determined. The destruction temperature of the dextran phosphate salt of the substance was found, and it was shown that the melting or destruction temperature of the active substance could not be recognized in the dextran phosphate salt.

Additionally it was shown that the destruction temperature of dextran phosphate was different from the destruction temperature of the dextran phosphate salt of the active substance.

Dextran phosphate has a destruction temperature of about 130–140° C.

Cyclobenzaprine-dextran phosphate:

DSC: Melting point of cyclobenzaprine was found to be 214.9° C.

The dextran phosphate salt of cyclobenzaprine has no melting point, but the substance starts to decompose at about 125° C.

This indicates that the active substance is not present as crystals in the mixture and that dextran phosphate and Cyclobenzaprine precipitate as a salt.

Polymyxin-dextran phosphate (pH 9):

DSC: Polymyxin has no melting point but starts to decompose at about 125° C.

The dextran phosphate salt of polymyxin has no melting point, but the substance starts to decompose at about 135° C.

This indicates that the active substance is not present as crystals in the mixture and that dextran phosphate and polymyxin precipitate as a salt.

Polymyxin-dextran phosphate (pH 5):

DSC: Polymyxin has no melting point but starts to decompose at about 125° C.

The dextran phosphate salt of polymyxin has no melting point, but the substance starts to decompose at about 140° C.

This indicates that the active substance is not present as crystals in the mixture and that dextran phosphate and polymyxin precipitate as a salt.

EXAMPLE 48

Analysis of Dextran Sulphate120000 Salts

The drug substances and the dextran sulphate salts of these substances were analysed as described below.

The dextran sulphate salt of the active substance was analysed by DSC. The melting point or destruction point of the active substance was determined. The destruction temperature of the dextran sulphate salt of the substance was found, and it was shown that the melting or destruction temperature of the active substance could not be recognized in the dextran sulphate salt.

Additionally it was shown that the destruction temperature of dextran sulphate was different from the destruction temperature of the dextran sulphate salt of the active substances.

Dextran sulphate 120 000 has a destruction temperature of about 150° C.

Bacitracin-dextran sulphate (120 kD):

DSC: the dextran sulphate salt of bacitracin has no melting point, but starts to decompose at about 125° C.

The destruction temperature of dextran sulphate is about 150° C. This indicates that dextran sulphate and bacitracin precipitate as a salt.

Quinidine-dextran sulphate (120 kD):

DSC: Quinidine melts at about 170° C., recrystallizes and melts again at about 180° C.

The dextran sulphate salt of quinidine has no melting point, but starts to decompose at about 140° C.

This indicates that quinidine is not present as crystals in the mixture and that dextran sulphate and quinidine precipitate as a salt.

EXAMPLE 49

Analysis of Dextran Sulphate12000 Salts

The drug substance and the dextran sulphate salt of the substance were analysed as follows.

The dextran sulphate salt of the active substance was analysed by DSC. The melting point or destruction point of the active substance was determined. The destruction temperature of the dextran sulphate salt of the substance was found, and it was shown that the melting or destruction temperature of the active substance could not be recognized in the dextran sulphate salt.

Additionally it was shown that the destruction temperature of dextran sulphate was different from the destruction temperature of the dextran sulphate salt of the active substance.

Dextran sulphate 12 000 has a destruction temperature of about 150° C.

Polymyxin-dextran sulphate (12 kD):

DSC: Polymyxin starts to decompose at about 125° C.

The dextran sulphate salt of polymyxin has no melting point, but does not start to decompose before about 140° C.

This indicates that polymyxin is not present as crystals in the mixture and that dextran sulphate and polymyxin precipitate as a salt.

Cyclobenzaprine-dextran sulphate (12 kD):

DSC: the melting point of cyclobenzaprine was found to be 214.9° C.

The dextran sulphate salt of cyclobenzaprine has no melting point, but does not start to decompose before about 155° C.

This indicates that cyclobenzaprine is not present as crystals in the mixture and that dextran sulphate and cyclobenzaprine precipitate as a salt.

What is claimed is:

1. A therapeutic compound which is a substantially water-insoluble salt of a mono to octa-saccharide sugar acid having oxyacid groups with a biologically active organic compound selected from the group consisting of aminoglycosides, tetracylines, polypeptides, glycopeptides and macrolides.

2. A compound as claimed in claim 1 wherein the saccharide acid is a monosaccharide sugar acid.

3. A compound as claimed in claim 1 wherein the saccharide acid is a disaccharide sugar acid.

4. A compound as claimed in claim 1 having a solubility of less than $10^{-2}$ mM/L in deionized water at ambient temperature.

5. A compound as claimed in claim 1 wherein said sugar acid has a ratio of acid groups to monosaccharide units of at least 2:1.

6. A compound as claimed in claim 1 wherein said sugar acid has a ratio of acid groups to monosaccharide units of at least 3:1.

7. A compound as claimed in claim 1 in sterile crystalline form.

8. A compound as claimed in claim 1 wherein said acid is a poly-O-sulphonic acid.

9. A compound as claimed in claim 8 wherein said acid is a disaccharide poly-O-sulphonic acid.

10. A compound as claimed in claim 9 wherein said acid is sucrose-octa-O-sulphonic acid.

11. A therapeutic compound which is a substantially water-insoluble salt of a mono to octa-saccharide sugar acid having oxyacid groups with a biologically active organic compound selected from the group consisting of aminoglycosides, tetracyclines, polypeptides, glycopeptides and macrolides, and a physiologically tolerable counterion.

12. A compound as claimed in claim 11 wherein said physiologically tolerable counterion is selected from the group consisting of alkali metal, alkaline earth metal, ammonium and aluminium ions.

13. A compound as claimed in claim 12 wherein said physiologically tolerable counterion is an aluminium ion.

14. A compound as claimed in claim 1 wherein said organic compound is selected from the group consisting of doxycyclin, diltiazam, cyclobenzaprine, bacitracin, noscapine, erythromycin, polymyxin, vancomycin, nortriptyline, quinidine, ergotamine, benztropine, verapamil, flunarizine and imipramine.

15. A compound as claimed in claim 14, being a sucrose-octa-O-sulphonic acid salt of a said organic compound.

16. A pharmaceutical composition comprising a biologically active organic compound in the form of a salt with a sugar acid having oxyacid groups together with at least one physiologically acceptable carrier or excipient, said salt being a substantially water-insoluble salt of a mono to octa-saccharide sugar acid with a biologically active organic compound selected from the group consisting of aminoglycosides, tetracylines, polypeptides, glycopeptides and macrolides.

17. A method of antibacterial treatment of a warm-blooded animal with an antibacterially effective amount of a biologically active organic compound selected from the group consisting of aminoglycosides, tetracylines, polypeptides, glycopeptides and macrolides to combat a condition responsive to said compound, said method comprising administering to said warm-blooded animal said effective amount of said organic compound in the form of a substantially water-insoluble salt with a mono to octa-saccharide sugar acid having oxyacid groups.

18. A method as claimed in claim 17 wherein said salt is administered perorally.

19. A method as claimed in claim 17 whereins aid salt is administered topically to a mucous membrane.

* * * * *